United States Patent
Ikeda (10) Patent No.: US 6,676,644 B2
(45) Date of Patent: Jan. 13, 2004

(54) SUCTION UNIT FOR MEDICAL APPLICATIONS

(76) Inventor: Yukio Ikeda, 5-10, Uemine 1-chome, Yono-shi, Saitama-ken, 338-0014 (JP)

( * ) Notice: Subject to any disclaimer, the term of this patent is extended or adjusted under 35 U.S.C. 154(b) by 400 days.

(21) Appl. No.: 09/729,432

(22) Filed: Dec. 5, 2000

(65) Prior Publication Data

US 2002/0068914 A1 Jun. 6, 2002

(51) Int. Cl.$^7$ ................................................ A61M 1/00
(52) U.S. Cl. ...................................................... 604/317
(58) Field of Search ................................ 604/317, 318, 604/319, 327; 128/765; 417/415

(56) References Cited

U.S. PATENT DOCUMENTS

| | | | | |
|---|---|---|---|---|
| 5,178,095 A | * | 1/1993 | Mein ........................ | 119/14.47 |
| 5,238,582 A | | 8/1993 | Hori et al. ................... | 210/749 |
| 5,466,229 A | * | 11/1995 | Elson et al. ................. | 604/317 |
| 5,720,722 A | * | 2/1998 | Lockridge ..................... | 604/74 |
| 6,056,731 A | * | 5/2000 | Koetke et al. ............... | 604/323 |
| 6,257,847 B1 | * | 7/2001 | Silver et al. ................. | 417/415 |
| 6,342,048 B1 | * | 1/2002 | Verkaart et al. ............. | 604/323 |
| 6,482,190 B1 | * | 11/2002 | Genese et al. .............. | 604/327 |

FOREIGN PATENT DOCUMENTS

| | | | | |
|---|---|---|---|---|
| EP | 0573117 | * | 6/1993 | ............ A61M/1/00 |
| WO | WO 90/00908 | * | 2/1990 | ............ A61M/1/00 |

* cited by examiner

*Primary Examiner*—Weilun Lo
*Assistant Examiner*—Michele Kidwell
(74) *Attorney, Agent, or Firm*—Armstrong, Kratz, Quintos, Hanson & Brooks, LLP (57) ABSTRACT

A suction unit comprises reciprocating change-over suction device 1 including tubular body 1a having with passage 2 and two branch passages 2a and 2b bifurcated from passage 2 connected to a suction apparatus. Cylinder 1b is movable in body 1a and has ventilation passages 4 and 5 and actuation plates 8 and 9 fixed to ends of cylinder 1b. Chambers 6 and 7 are connected to the end portions of body 1a with closing members closing openings of the chambers. Elastic containers 10 and 11 are contained in chambers 6 and 7, openings of these containers being fixed to inner surfaces of closing members 14 and 15. Closed valves 12 and 13 are on chambers 6 and 7 and suction tubes 18a and 18b are connected to inflow passages 16a and 16b of members 14 and 15 and, at another end, are connected to common suction tube 18. Discharging tubes 19a and 19b are connected to outflow passages 17a and 17b of members 14 and 15 and, at another end, to storage container 20.

14 Claims, 7 Drawing Sheets

SUCTION UNIT FOR MEDICAL APPLICATIONS

TECHNICAL FIELD PERTAINING TO THE INVENTION

The present invention relates to a suction unit for medical applications.

BACKGROUND OF THE INVENTION

Figure 7:
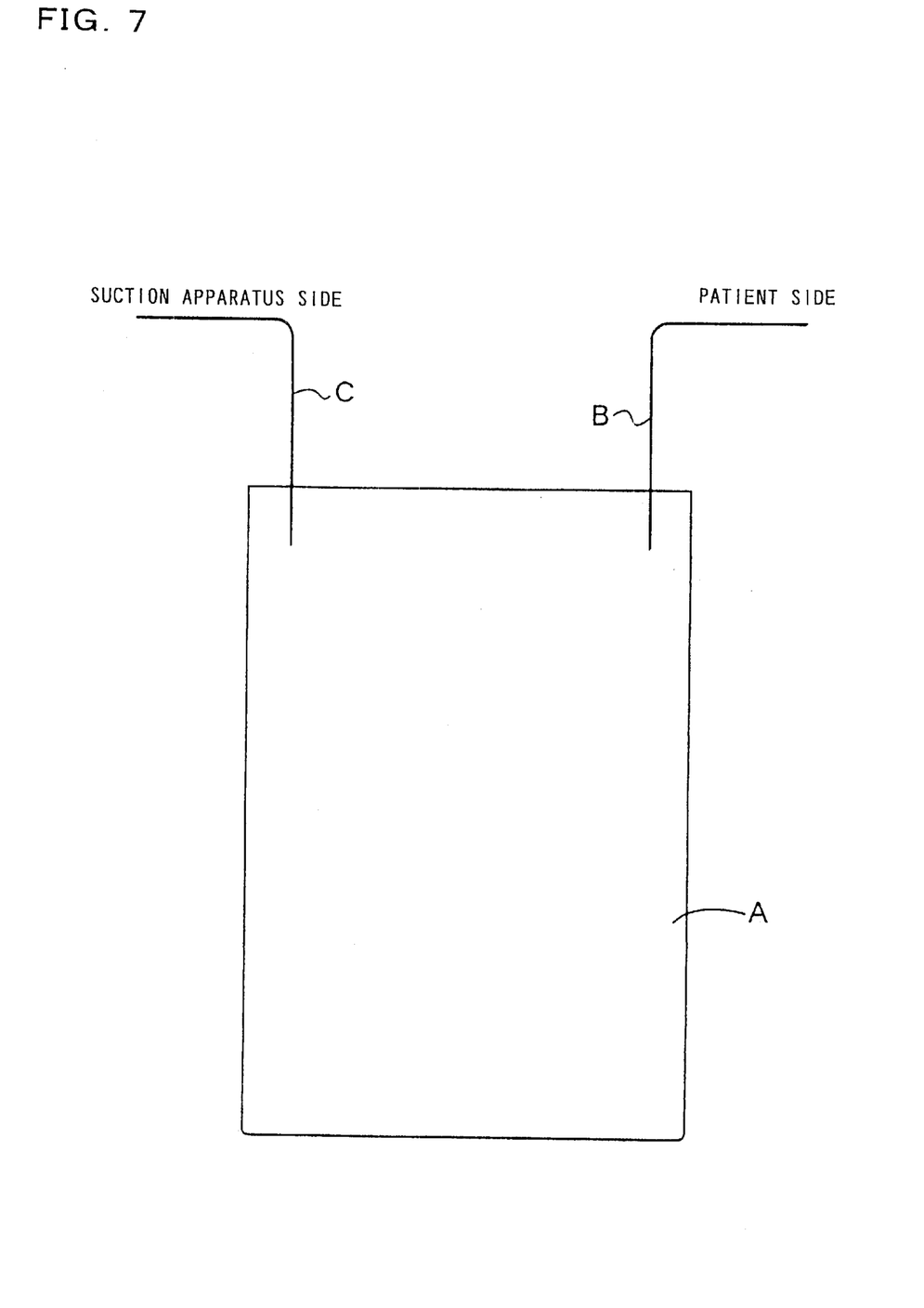
FIG. 7 is a partial sectional front view of a conventional suction unit.

A conventional suction unit for a medical application, is shown in FIG. 7. This unit comprises a closed storage container A for storing waste fluids or liquids such as phlegm, blood, pus, bodily fluids such as secreting fluid; fluids containing solids; and such as feces in the intestines and the like from patients; and fluids after cleaning the lesions or affected parts of patients with a physiological salt solution or the like, all of which are generated during medical care or surgery. The unit further includes a waste fluid suction tube B connected to one side of the upper portion of container A for sucking a waste fluid from a patient and a suction tube C which is connected to the other side of the upper portion of the container for sucking air in the closed waste fluid storing container by a suction apparatus connected to the other end of suction tube C. This unit is used in such a manner that the suction apparatus such as a vacuum pump connected to the one end of the suction tube C is actuated and the outer end of the waste fluid suction tube B is applied to a lesion of a patient. As a consequence, the air in the waste fluid storage container A and the waste fluid suction tube B is exhausted or evacuated, and thus the waste fluid from the patient passes through the waste fluid suction tube B and into the waste fluid storage container A. There are two types of waste fluid storage containers, i.e., a reusable type container made of glass and a disposable container made of synthetic resin.

However, the above-mentioned conventional suction unit has several problems because the waste fluid storing container is connected directly to the vacuum pump.

In particular, during operation of the suction unit, when air in the waste fluid storage container A is evacuated by the vacuum pump, some of the waste fluid flowing into the storing container from the waste fluid suction tube B and some of the waste fluid stored in the waste fluid storage container are converted into mist by the suction force of the vacuum pump. The mists are sucked into the vacuum pump and may be released to the open air from the vacuum pump through the suction tube C by the exhaust operation thereof. Accordingly, the vacuum pump, accessories thereof such as a suction force regulator and others connected thereto are contaminated with the mists, and, at the same time, the inner and outer atmospheres of a room in which the vacuum pump and accessories thereof are located are contaminated with the mists.

As a countermeasure, to the above, a filter may be interposed in the evacuation path, for instance, in the middle of the suction tube C. However, such a filter not only cannot completely remove bacteria and viruses contained in the mists of the waste fluids, but also the suction operation cannot be carried out by the desired large negative pressure. In addition, if the filter becomes clogged so that the suction force is decreased remarkably, a smooth operation is not impossible.

Furthermore, if a bag-type container such as a disposable container made of plastic is used, it cannot withstand the desired vacuum pressure and becomes deformed so as to be flat or broken; Thus, the waste fluid container has to be limited to a container durable to a negative pressure applied thereto.

In view of foregoing problems with the conventional suction unit, it is desired to provide a suction unit that does not contaminate the suction apparatus and the environment and makes it possible to suck and store a waste fluid from a patient smoothly, sanitarily and efficiently, and also makes it possible to use various types of the storage containers regardless of whether such containers are of hard or soft materials.

SUMMARY OF THE INVENTION

It is therefore an object of the present invention to provide a suction unit for medical applications which solves the problems associated with conventional suction units, and it comprises a reciprocating type change-over suction device, the suction device being composed of a cylinder holding tubular body which is provided with a single passage and left and right branch passages bifurcated from the single passage for connecting a suction apparatus, and a cylinder which is held slidably by the cylinder holding tubular body and which is provided with left and right ventilation passages, left and right closed chambers connected to left and right end portions of the cylinder holding tubular body, left and right elastic containers which are contained in the left and right closed chambers and of which the mouth edges are airtightly attached to the inner surfaces of left and right closing members, left and right actuation plates which are connected to the left and right end portions of the cylinder and contained in the left and right closed chambers, left and right normally-closed type valves installed on the left and right closed chambers, left and right waste fluid suction tubes which are connected at one end portions thereof to left and right waste fluid inflow passages penetrating the left and right closing members and at the other end portions thereof to a single waste fluid suction tube which is applicable to a lesion of a patient, and left and right waste fluid discharging tubes which are connected at one end portions thereof to left and right waste fluid outflow passages penetrating the left and right closing members and at the other end portions thereof to a waste fluid storage container.

Another object of the present invention is to provide a suction unit which can be used by simply assembling, and it comprises an assembly composed of the following (a) and (b) constructional bodies:

(a) a suction-system constructional body comprising the suction device, the left and right actuation plates connected to the left and right end portions of the cylinder, the left and right chambers which are composed of left and right end plates and left and right transparent cylindrical walls attached at the inner end portions thereof to the left and right end walls to form left and right chambers of which the mouths are open at the outer sides thereof, and the left and right normally closed type valves installed on the left and right chambers.

(b) a waste fluid-system constructional body comprising the closed waste fluid storing container, the left and right waste fluid discharging tubes connected to the upper inside space portion of the closed waste fluid storing container, the left and right closing members connected to the outer end portions of the left and right waste fluid discharging tubes, the left and right suction tubes which are connected at one ends portions thereof to the left and right closing members and at the other end portions to the single suction tube.

Further another object of the present invention is to provide a suction unit which ensures respective air communications between the left and right air passages of the cylinder and the left and right branch passages, in the left and right reciprocating movements of the cylinder, and it is characterized in that the cylinder is provided with annular grooves which communicate with left and right air holes.

Further another object of the present invention is to provide a suction unit which can be used suitably and favorably near a patient's bed, and it is characterized in that it is mounted on a stand.

Further another object of the present invention is to provide a suction unit which makes it possible to store a waste fluid up to a predetermined amount in the waste fluid storage container, and it is characterized in that the waste fluid storage container is a disposable plastic container, and part of the closed upper end portion of the waste fluid storage container is provided with a filter.

Yet another object of the present invention is to provide a suction unit of which the waste fluid storage container is easy to mount on the stand and remove therefrom, and it is characterized in that the disposable container comprises a container in the shape of a bag which has a capacity in the range of from 3000 ml to 8000 ml, graduations on the surface thereof, and a plural number of hanging holes made in a sealed long and narrow portion provided at the upper portion thereof.

DETAILED DESCRIPTION OF THE PREFERRED EMBODIMENTS OF THE INVENTION

Preferred embodiments of the present invention will be described with reference to the accompanying drawings in the following.

A fundamental concept of the present invention is to avoid conventional practices where the suction apparatus is connected through the suction tube to the waste fluid storage container, and the suction force produced by the exhaust operation of the suction apparatus is applied directly to the waste fluid container so as to suck a waste fluid from a lesion of a patient through the waste fluid suction tube connected to the container and store it in the container. Instead, provided is a suction unit for medical applications or using an elastic container interposed between the suction apparatus and the waste fluid storage container, so that the connection between the suction apparatus and the waste fluid storage container may be cut off from the waste fluid, and the suction force of the suction device may not be applied to the waste fluid storing container. However, the waste fluid from the patient may be collected in the elastic container expanded by the suction force of the suction apparatus, and then the elastic container may be compressed, that is, contracted by a positive pressure of an atmospheric air, so as to discharge the collected waste fluid into the waste fluid storing container. Thus, the foregoing process of the operations is repeated on the left side and the right side alternately for a desired operation time.

Figure 1:
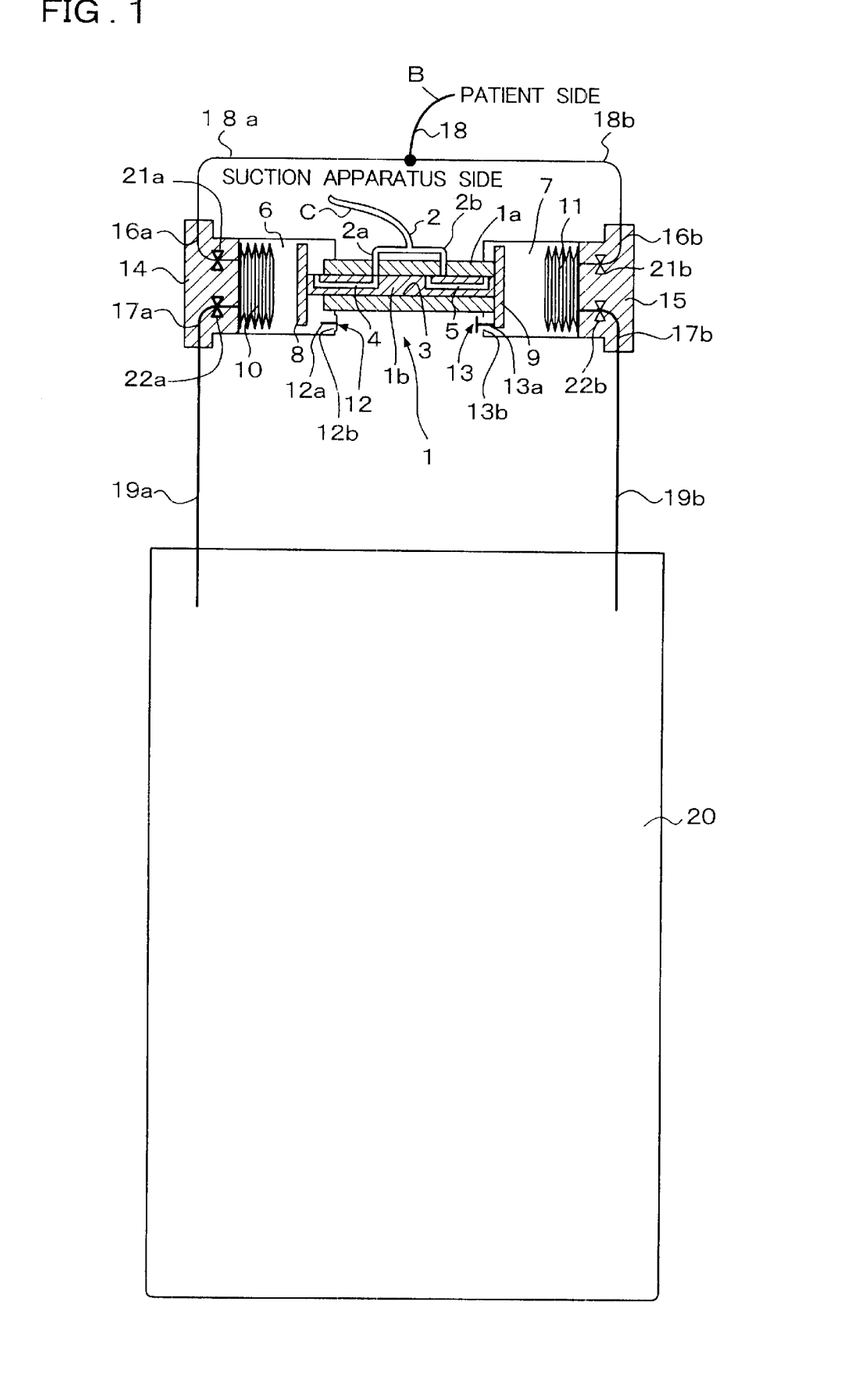
FIG. 1 is a schematic front view showing one embodiment of a suction unit for medical applications according to the present invention.

FIG. 1 shows a diagrammatic view of one embodiment of a suction unit according to the present invention. In the drawings, numeral 1 denotes a reciprocating type suction change-over device connected to a suction tube C which in turn is connected to a suction apparatus such as a vacuum pump (not shown). The reciprocating type suction change-over device 1 comprises a cylinder holding tubular body 1a includes a single suction passage 2, which is to be connected at its outer end opening to the suction tube C, and two branch passages 2a and 2b bifurcated from the suction passage 2, and a cylinder 1b inserted in a central axial hole 3 of the cylinder holding tubular body 1a and is held therein so as to be slidable in the hole. The cylinder 16 is also provided with left and right ventilation passages 4 and 5. Numerals 6 and 7 denote closed chambers disposed respectively on the left side and the right side of the suction change-over device 1. The cylinder 1b is positioned within the cylinder holding tubular body 1a of the suction change-over device 1 such that either one of the left and right ventilation passages 4 and 5 may be brought in communication with either one of the left and right branch passages 2a and 2b in the cylinder holding tubular body 1a and either one of the left and right closed chambers 6 and 7, while the other one of the left and right ventilation passages 4 and 5 is not in communication with the other one of the left and right branch passages 2a and 2b and the other one of the left and right closed chambers 6 and 7.

The position as illustrated shows where the cylinder 1bis such that the left ventilation passage 4 is positioned to allow the mutual communications between the left branch passage 2a and the left closed chamber 6, while the right ventilation passage 5 thereof is positioned to cut off the mutual communications between the right branch passage 2b and the right closed chamber 7, so that left and right actuation plates 8 and 9, which are fixed to both ends of the cylinder 1b, and left and right elastic containers 10 and 11, which are expandable by respective negative pressures alternately generated in the left and right closed chambers 6 and 7 by the suction operation of the suction apparatus such as a vacuum pump or the like (not shown), are contained in the respective left and right closed chambers 6 and 7 so as to face each other.

The left and right closed chambers 6 and 7 are also provided respectively with left and right normally closed type valves 12 and 13. Valves 12 and 13 are opened in response to a collision with the respective left and right actuation plates 8 and 9 in the course of the respective backwards movements thereof as pushed by alternate expansions of the elastic containers 10 and 11 which alternately allow the atmospheric air to enter the closed chambers 6 and 7. Further, the left and right closed chambers 6 and 7 are provided with left and right closing members 14 and 15 which airtightly close the mouths of the chambers. The interiors of the left elastic container 10 is connected to a waste fluid inflow passage 16a and a waste fluid outflow passage 17a and right elastic container 11 is connected to a waste fluid inflow passage 16b and a waste fluid outflow passage 17b which respectively penetrate the left and right closing members 14 and 15. Passages 16a and 16b respectively are connected to a waste fluid suction tube 18a and a waste fluid discharging tube 19a and the waste fluid outflow passages 17a and 17b respectively are connected to a waste fluid suction tube 18b and a waste fluid discharging tube 19b. The outer end portions of the left and right waste fluid suction tubes 18a and 18b are connected to a single waste fluid suction tube 18 which may be applied to a lesion or affected part of a patient. Further, the outer end portions of the left and right waste fluid discharging tubes 19a and 19b are connected to a sealed waste fluid storing container 20.

The left and right waste fluid inflow passages 16a and 16b respectively are provided with left interposed and right normally closed type valves 21a and 21b which are opened in response to respective expansions of the left and right elastic containers 10 and 11. The left and right waste fluid outflow passages 17a and 17b respectively are provided with interposed left and right normally closed type valves 22a and 22b which are opened in response to respective contractions of the left and right elastic containers 10 and 11.

Next, the operation of the foregoing suction unit according to the present invention will be explained in the following:

First, the suction apparatus, the suction pump as usual is actuated, and the free end of the waste fluid suction tube 18 is applied to the lesion of a patient. Air in the closed chamber 6 on the left side in the drawings, hereafter referred to as "left chamber 6" is removed through the left ventilation passage 4 of the cylinder 1b and the left branch passage 2a, so that a negative pressure is generated in the left chamber 6. Consequently, the elastic container 10 in the left chamber 6 is expanded by the negative pressure, and the normally closed type valve 21a is opened in the progress of the expansion thereof to bring the elastic container 10 in communication with the waste fluid inflow passage 16a. As a result, a negative pressure is generated both in the waste fluid suction tube 18, the forward end opening being applied to the lesion under a closed condition, and in the waste fluid suction tube 18a connected to the suction tube 18. Therefore, the waste fluid in the lesion is sucked through the suction tubes 18 and 18a and is introduced into the expanded elastic container 10 by the suction operation in the same principle of the operation as a spuit or an injector.

Meanwhile, during expansion of the elastic container 10, the elastic container collides with the left actuation plate 8 positioned opposite thereto, and pushes the plate. Thereby, the actuation plate 8 is forced to move rightwards in the drawing, and also the cylinder 1b, integral with the actuation plate 8 is moved rightwards in conjunction with the successive rightward movement of the actuation plate 8. As a result, the communication between the left chamber 6 and the branch passage 2a through the left ventilation passage 4 of the cylinder 1b is cut off, and accordingly the suction force of the vacuum pump on the left chamber 6 is interrupted. After sufficient movement of actuation plate 8, the plate acts on a rod 12a of the normally closed type valve 12 opposite thereto to open the valve, and allow open air, that is, atmospheric air, to flow into the left chamber 6 through an intake opening 12b. Thus, the negative pressure in the left chamber 6 returns to a positive pressure, that is, atmospheric pressure, and the expanded elastic container 10 is then pushed and contracted by the positive pressure. The compression force of container 10 causes the normally closed type valve 21a to close the waste fluid inflow passage 16a, and also, causes the normally closed type valve 22a closing the waste fluid outflow passage 17a to open, so that the waste fluid collected in the elastic container 10 is discharged and is sent under pressure through the waste fluid discharging tube 19a into the airtightly closed waste fluid storage container 20.

On the other hand, in conjunction with rightward movement of the foregoing cylinder 1b, the actuation plate 9 connected to the right end thereof begins to be moved rightwards in the drawing. When a rod 13a of the normally closed type valve 13 which has been brought in an opened condition by pushing the actuation rod 13a thereof by the actuation plate 9 is moved to separate from the actuation rod 13a, an intake opening 13b is closed automatically by the normally closed type valve 13. Thus, the communication between the right chamber 7 on the right side, hereafter referred to as "right chamber," is cut off, so that the right chamber 7 becomes an airtight chamber.

When the cylinder 1b is further moved rightwards, the right ventilation passage 5 is positioned to allow communication between the right chamber 7 and the right branch passage 2b. Then the air confined in the right chamber 7 is exhausted by the suction force of the vacuum pump, so that a negative pressure is produced therein. The right elastic container 11 is expanded by the negative pressure, and during the expansion of the volume of the elastic chamber 11, the normally closed type valve 21b which closes the waste fluid inflow passage 16b is opened. The waste fluid from the patient is sucked through the waste fluid suction tubes 18 and 18b and the waste fluid inflow passage 16a and is collected in the expanded elastic container 7.

Further expansion of the elastic container 11 causes the container to collide with the actuation plate 9 and push it leftwards. When finally the actuation plate 9 is moved to the extreme left end, that is, to the original position, so that the cylinder 1b which is integral with the actuation plate 9, is moved to the left, the communications between the right chamber 7 and the right ventilation passage 2b through the right branch passage 2b is cut off. At the same time the actuation plate 9 pushes the valve rod 13a of the normally closed type valve 13 so as to open the valve 13, and allow atmospheric air to be introduced into the right chamber 7 through the air intake opening 13b. Consequently, the negative pressure of the right chamber 7 turns into a positive pressure, and the positive pressure compresses the expanded elastic chamber 11 which opens the normally closed type valve 22b. This closes the waste fluid outflow passage 17b and causes the collected waste fluid in the elastic container 11 to be discharge under pressure through the waste fluid discharging tube 19 and then stored in the waste fluid storage container 20.

Further, in the meantime, the leftward movement of the cylinder 1b again allows the communication between the left chamber 6 and the branch passage 2a through the left ventilation passage 4 and, at the same time, the left actuation plate 8 separates from the valve rod 12a of the normally closed type valve 12. Thus, the air intake opening 12b is closed automatically and the communication between the left chamber 6 and the open air is cut off, and consequently a negative pressure again is generated in the left chamber 6.

Thus, the suction change-over device 1 operates such that one of the left and right chamber 6 and 7 is brought in a negative pressure condition and the other chamber is brought in a positive pressure condition, then the other chamber is brought in a positive pressure condition while the other chamber is brought in a negative pressure condition by the alternate leftward and rightward movements of the reciprocation of the cylinder 1b. Such alternate reciprocating movements are repeated a desired number of times. Thus, withdrawing the waste fluid from the patient and storing the withdrawn waste fluid into the waste fluid storage container can be carried continuously and sanitarily without contamination of the suction device, the suction apparatus or the environment with the waste fluid.

In greater detail, the following advantages can be realized by the suction unit according to the present invention since:

(a) Since the suction apparatus is not in communication with the suction tubes, the elastic containers, the waste fluid discharging tubes and the waste fluid storage container, the disadvantage associated with a conventional suction unit as mentioned above can be avoided. Thus, the suction of the waste fluid from a patient and storage of the sucked waste fluid into the waste fluid storing container can be carried out continuously without contaminating the suction device, the suction apparatus or the environment with the waste fluid, and therefore suction can be conducted sanitarily, smoothly and efficiently for a desired time.

(b) The interposition of a filter in the suction side is not needed, and therefore a desired higher suction force can be applied by the suction apparatus.

(c) Since there is no fear of deforming, flattening or breaking the waste fluid storage container, a soft type container such as a soft plastic bag which does not withstand a negative pressure can be used.

Figure 2:
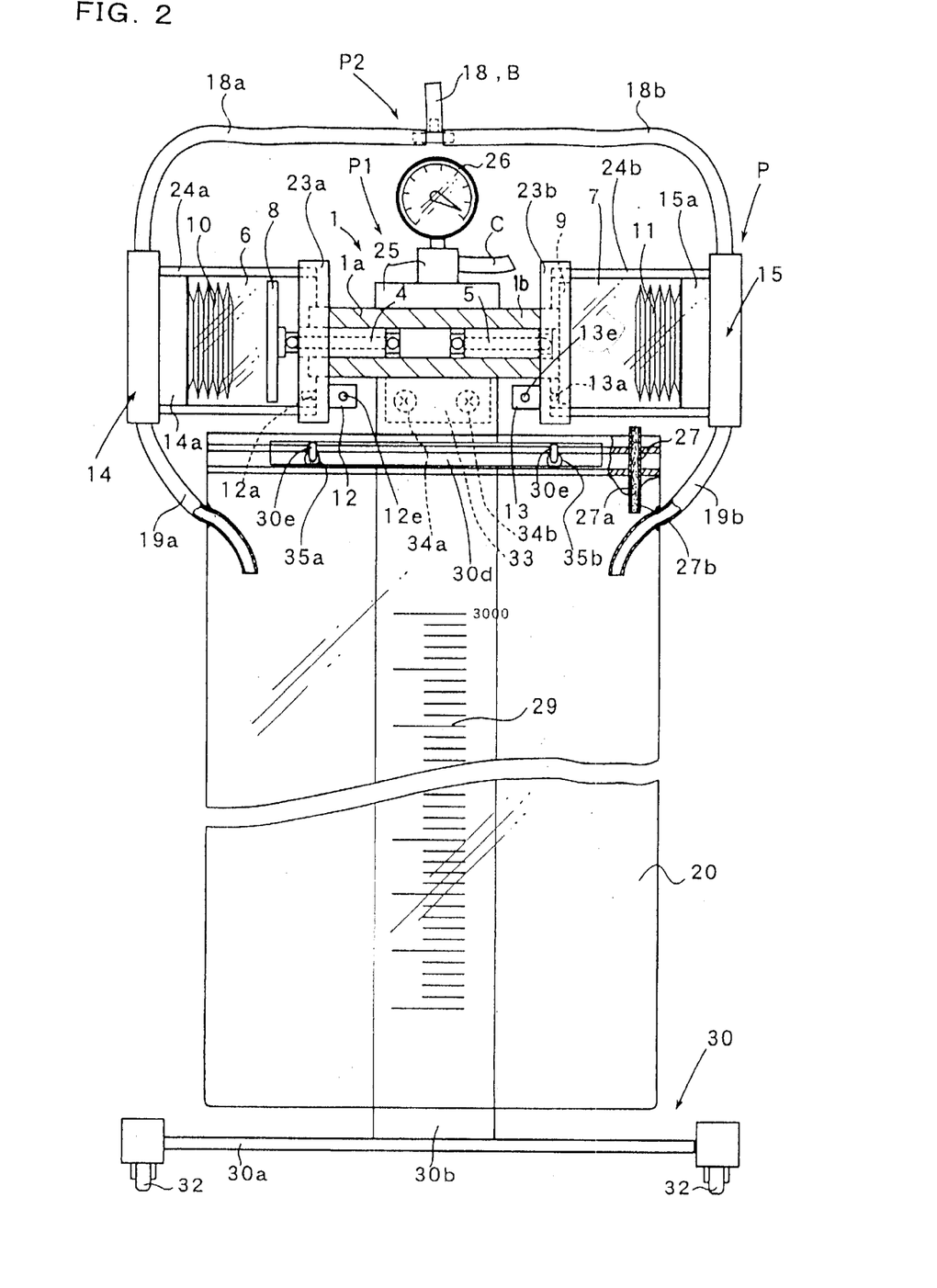
FIG. 2 is a front view of a preferred and more concrete suction unit for medical applications according to the present invention which is mounted on a stand.
Figure 3:
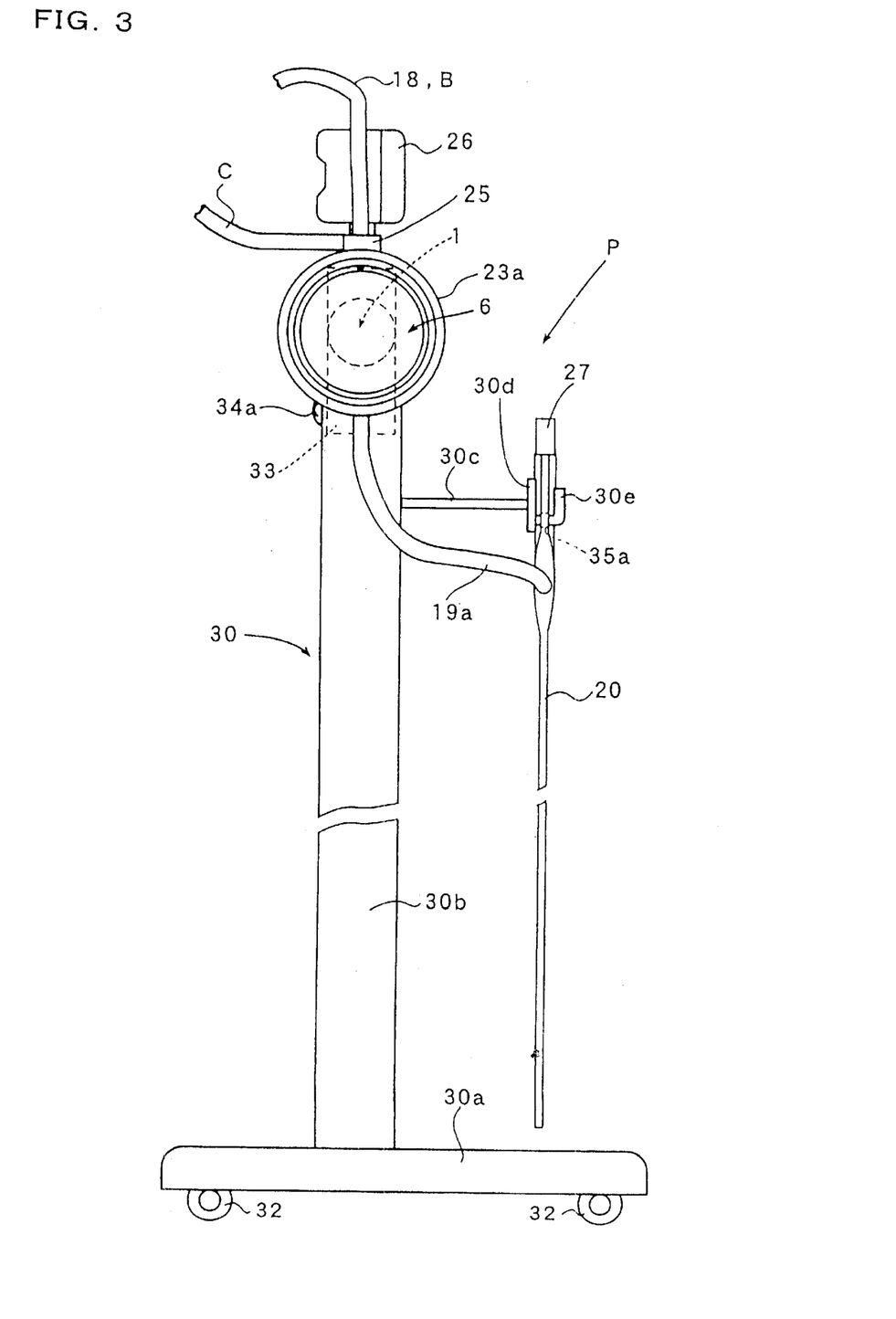
FIG. 3 is a side view of the unit as shown in FIG. 2.
Figure 4:
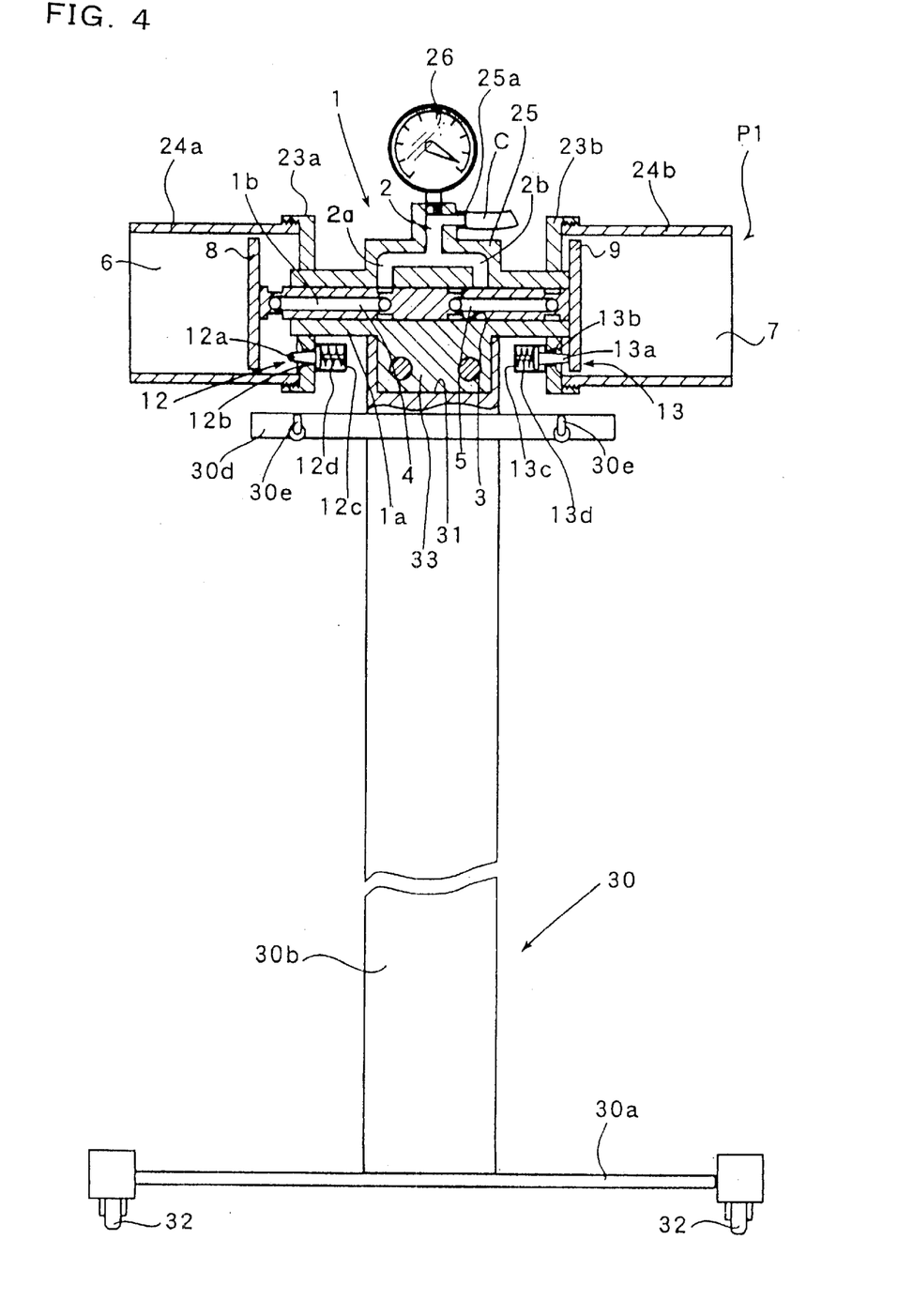
FIG. 4 is a sectional front view a suction system body, which is a part of the suction unit according to the present invention as shown in FIG. 2, as mounted on the stand.

FIG. 2 and FIG. 3 show a more concrete embodiment of the suction unit as shown in FIG. 1 according to the present invention. Suction unit P preferably is constructed by detachably assembling a suction system body P1 as shown in FIG. 4 and a fluid system body P2 as shown in FIG. 5 one with each other. At the time of use, body P2 is mounted on a stand 30 as shown in FIG. 4, which a mobile or transfer type is preferable as shown in FIG. 3, which will be explained more in detail below.

The suction system body P1 comprises mainly the reciprocating-type suction change-over device 1 which is composed of the cylinder holding tubular body 1a made of a corrosion-resistant metal such as stainless steel or the like and the cylinder 1b which is made of the same corrosion-resistant metal. Cylinder 1bis longer than the cylindrical holding tubular body 1a and is held therein and slidably movable left and right within the tubular body. In addition, cylinder holding tubular body 1a is provided with left and right end plates 23a and 23b which also are made of stainless steel or the like and are fixed to the outer peripheral surfaces of both end portions of the body 1a such that they are mounted thereon at central holes thereof and are fixed thereto by screwing or welding. Cylinder holding tubular body 1a is provided with left and right transparent cylindrical walls 24a and 24b made of glass or plastics which are airtightly fixed to the left and right end plates 23a and 23b by screwing or welding together. Formed are left and right chambers 6 and 7 open at their outer ends and which have inner end walls formed by the left and right end plates 23a and 23b and which have the left and right actuation plates 8 and 9 fixed to the both end surfaces of the cylinder 1bcontained on the inner sides thereof. In addition, left and right normally closed type valves 12 and 13 are installed on the left and right end plates 23a and 23b of the left and right chambers 6 and 7 so as to face the back surfaces of the respective actuation plates 8 and 9.

Figure 6A:
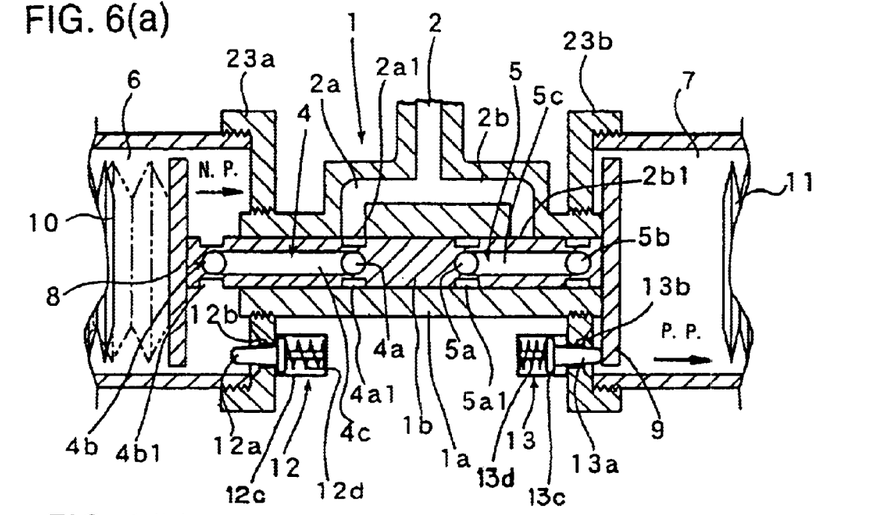
FIG. 6(a) is a sectional front view of a main part of the suction unit for illustrating operation thereof which shows a cylinder of a reciprocating type change-over suction device located at the extreme left end.
Figure 6B:
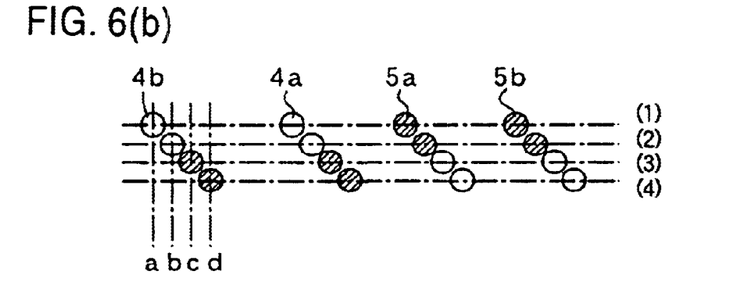
FIG. 6(b) is a diagram showing respective steps of communication and non-communication of air holes with left and right branch passages and left and right closed chambers in the course of shifting the cylinder of FIG. 6(a) from the extreme left end to the extreme right end.
Figure 6C:
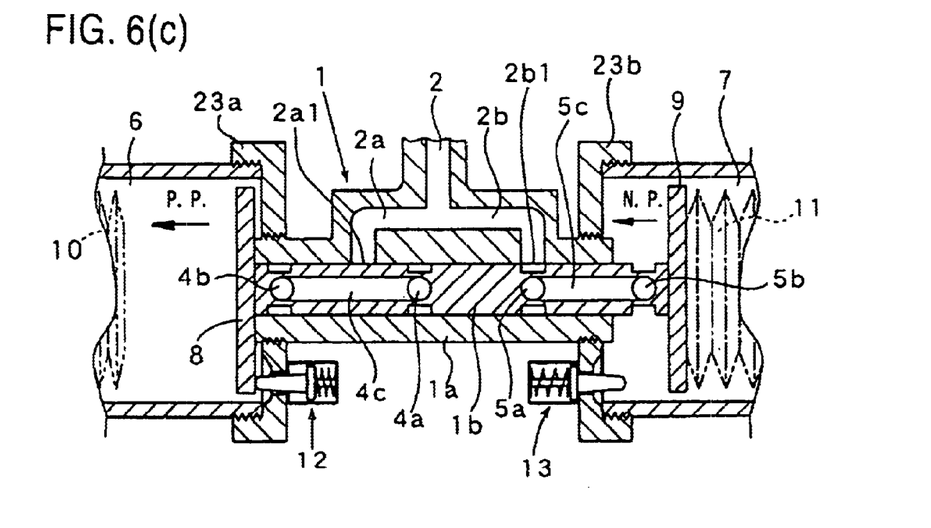
FIG. 6(c) is a sectional front view of the main portion of the suction unit which shows the cylinder located at the extreme right end.

In the illustrated embodiment shown in FIG. 6, the cylindrical outer surfaces of both end portions of the cylinder holding tubular body 1a are provided with external threads, and the central holes of the left and right end plates 23a and 23b are formed into threaded holes. Thus, the left and right end plates 23a and 23b are threaded onto the threaded end portions of the cylinder holding tubular body 1a. Further, the outer peripheral edges of the left and right end plates 23a and 23b are provided with respective circular peripheral flanges, the inner surfaces of which being provided with threads. The threaded outer end portions of the left and right transparent cylindrical walls 24a and 24b are threaded into the left and right threaded peripheral flanges of the left and right end plates 23a and 23b, thereby forming the left and right chambers 6 and 7.

In addition, as clearly shown in FIG. 4, the cylinder holding tubular body 1a is provided with a metallic protrusion 25 integral therewith which projects upwardly from the center portion of the upper surface of the body. The single suction passage 2 opens at the central part of the upper surface of the protrusion 25 and extends vertically and upwardly in the protrusion 25. The left and right branch passages 2a and 2b which are bifurcated from the single suction passage 2 and which are brought in alignment with the left and right ventilation passages 4 and 5 are also contained in protrusion 25. A tubular opening portion 25a which communicates with the suction passage 2 and connects the suction tube C is provided in the side surface of the protrusion 25 so that the suction tube C, the outer end of which is connected to the suction apparatus, for instance, a vacuum pump (not shown) may be connected to the protrusion 25. In addition, a vacuum gage 26 is screwed into a threaded hole formed in the upper end of the suction passage 2. The suction apparatus may be provided in general with a suction force regulator (not shown), and it is generally preferable that the suction force is regulated therewith as desired from a low suction force of −150 mm Hg or less to a middle or high suction force of −150 mm Hg or more.

Furthermore, the left and right actuation plates 8 and 9 fixed to both ends of the cylinder 1b, which is generally in a round form in cross-section and is inserted through and slidably movable along the axial center hole 3 of the cylinder holding tubular body 1a, are in the form of a disk and are made of metal, for instance, and are fixed to both ends of the cylinder 1b by welding, mating threads, with screws, or the like.

Furthermore, in the foregoing embodiment, the suction passage 2 and the branch passages 2a and 2b are formed by passages within the protrusion 25 which integral with the cylinder holding tubular body 1a. Instead of the protrusion 25, a tube in a Y-shape not shown may be detachably connected to the tubular opening 25a of the suction passage 2 of the cylinder holding tubular body 1a.

The left and right normally closed type valves 12 and 13 respectively comprise metal housings 12c and 13c which are attached by welding, with screws, or the like, to the left and right end walls 23a and 23b of the left and right chambers 6 and 7. The valves 12 and 13 further include springs 12d and 13d provided in the housings 12c and 13c and left and right valve rods 12a and 13a which are pushed by the springs 12d and 13d to normally or ordinarily close air intake openings 12b and 13b in the left and right end plates walls 23a and 23b. When the valve rods 12a and 13a are pushed by the corresponding actuation plates 8 and 9, the normally closed type valves 12 and 13 open to allow the atmospheric air to flow into the housings 12c and 13c through air introducing openings 12e and 13e made in the housings 12c and 13c and further into the chambers 6 and 7 through the air intake openings 12b and 13b. Consequently, the interiors of the left and right chambers 6 and 7 are brought to the positive pressure of the atmosphere.

In the illustrated embodiment, the leftward and rightward movements of the reciprocating cylinder 1b are so regulated to be within a predetermined distance so that when the back surfaces of the actuation plates 8 and 9 collide with both the ends of the cylinder holding tubular body 1a, the leftward movement and the rightward movement of the cylinder 1b are restrained.

Figure 5A:
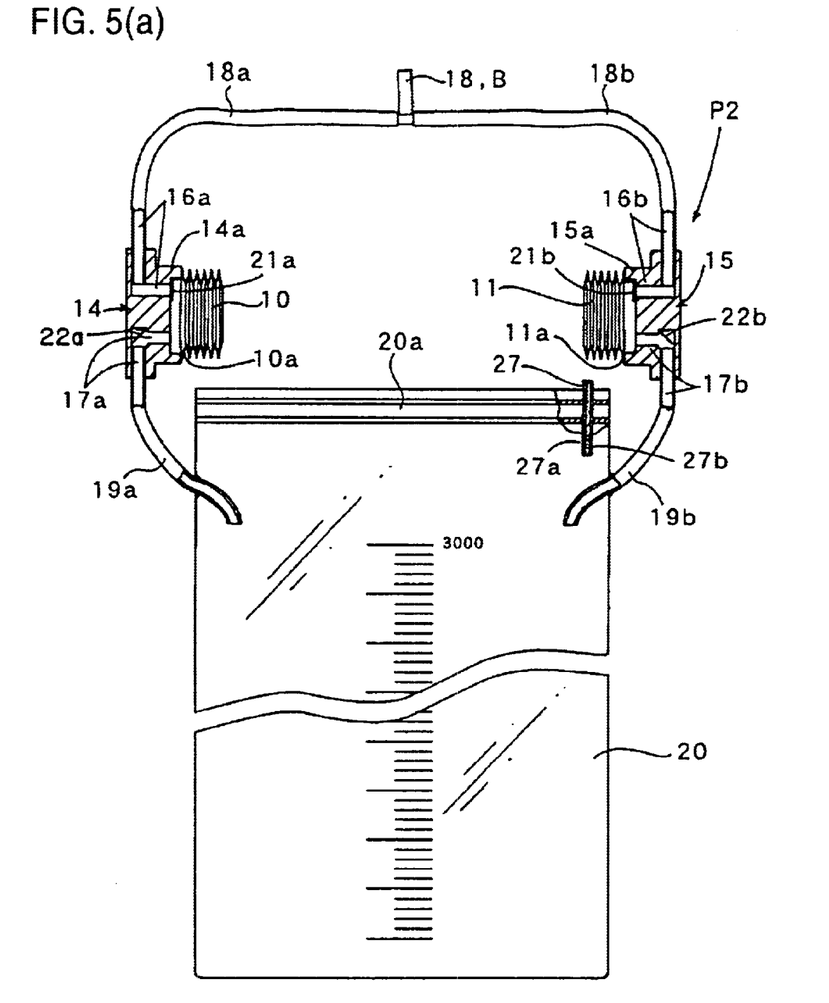
FIG. 5(a) is a partial sectional front view of a waste fluid system body, forming a part of the suction unit according to the present invention.
Figure 5B:
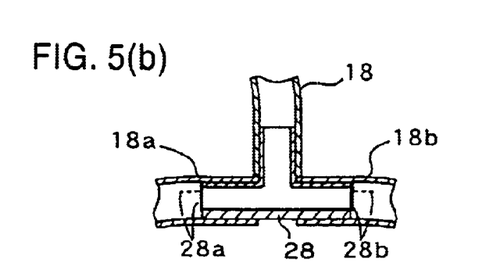
FIG. 5(b) is a sectional front view of part of the waste fluid system body as shown in FIG. 5(a)

The waste fluid system constructional body P2 primarily comprises the airtightly closed waste fluid storage container 20 and, in addition, the waste fluid discharging tubes 19a and 19b which are disposed on the left and right and communicate with the upper space of the interior of the container 20. The outer end portions of the left and right waste fluid discharging tubes 19a and 19b connect to the left and right closing members 14 and 15 so as to communicate with the left and right waste fluid outflow passages 17a and 17b penetrating the left and right closing members 14 and 15. The left and right closing members 14 and 15 are provided with left and right circular closure walls 14a and 15a formed integrally therewith and which protrude. The left and right closing members 14 and 15 are adapted to be mounted in and airtightly close the mouth openings of the left and right chambers 6 and 7, and, in addition, the peripheral edges 10a and 11a of the mouth openings of the left and right elastic containers 10 and 11 are airtightly fixed to the inner surfaces of the left and right circular closure walls 14a and 15a.

One end portion of the left and right waste fluid suction tubes 18a and 18b are connected to the left and right closing members 14 and 15 so as to communicate with the waste fluid inflow passages 16a and 16b penetrating the left and right closing members 14 and 15. In addition, the left and right waste fluid suction tubes 18a and 18b are connected to the single common waste fluid suction tube 18 which is to be applied to a lesion of a patient.

Regarding the waste fluid storage container 20, in general, a disposable container made of a hard or soft synthetic resin is preferably used. In the illustrated embodiment, a soft transparent plastic bag made of polyethylene or the like is used. The upper peripheral edge thereof is airtightly closed by heat sealing to make a sealed band portion 20a in the shape of a band having a predetermined broad width so that the container can be used as a sealed waste fluid storing container. In this case, it is generally preferable that the closed or sealed container be provided with a filter. One example of the closed container of this type is made such that, in the foregoing heat sealing operation, a plastic short tube 27 packing a filter member 27b therein is inserted through one side part of the sealed band portion 20a and is airtightly fixed thereto by heat sealing therearound. With such a provision, air in the upper space of the closed container 20 may be gradually discharged through the filter member 27b to the outside in accordance with an increase in the waste fluid which is gradually stored in the closed container 20 so that a predetermined amount of the waste fluid may be stored smoothly therein and air in the closed container 20 may be discharged to the outside sanitarily.

Also with regard to the waste fluid storage container 20, a desired volume thereof may be varied from 300 ml to 8000 ml. In this case, for the height of a stand 30 for supporting the container 20, the stand 30 with a height corresponding to a height of the selected container 20 is selectively used.

The left and right waste fluid discharging tubes 19a and 19b which are connected with the upper space of the container 20 are soft transparent plastic tubes made of polyethylene or the like. The lower portions of these tubes 19a and 19b are passed through left and right holes of the upper portion of the container 20, and are airtightly fused therearound by heat sealing to the inner peripheries of the holes, and are extended upwardly on the exterior by a desired length. The inner diameter of each of the tubes 19a and 19b may be generally in the range of 6 mm to 12 mm, and the length thereof from each of the left and right closing members 14 and 15 to the container 20 may be within the range of 10 cm–20 cm. The outer end portions of the left and right waste fluid discharging tubes 19a and 19b are fixedly connected to the waste fluid outflow passages 17a and 17b of the left and right closing members 14 and 15.

The closing members 14 and 15 may be moldings of synthetic resin in the form of a thick disk, and the left and right closure walls 14a and 15a in the disk form protruding from the inner surfaces thereof are formed by molding therein integrally with the molded closing members 14 and 15. The inner ends of the left waste fluid inflow passage 16a and the left waste fluid outflow passage 17a, which are disposed above and below and extend through the left closing member 14 integral with the closure wall 14a, and the inner ends of the right waste fluid inflow passage 16b and the right waste fluid outflow passage 17b, which are disposed above and below and extend through the right closing member 15 integral with the closure wall 15a, are in communication with the left elastic container 10 and the right elastic container 11, respectively.

In the illustrated embodiment, the elastic containers 10 and 11 are bellows types made of plastics or the like, and the volume of each may be in the range of 200 ml to 300 ml, for example. The edges on the open sides of the left and right elastic containers 10 and 11 are fixed by fusing them to the inner surfaces of the left and right closure walls 14a and 15a.

The normally closed type valves 21a and 21b are composed of circular thin plates made of synthetic resin or the like. The upper parts thereof are fixed by fusing them to the upper parts of the left and right closure walls 14a and 15a surrounding the circular ports of the inner ends of the waste fluid inflow passages 16a and 16b. The left and right waste fluid inflow passages 16a and 16b may be normally closed by the hanging the lower parts of the normally closed type valves 21a and 21b and the normally closed type valves 21a and 21b may be opened by the negative suction pressure generated at the time of the expansion of the elastic containers 10 and 11.

The normally closed type valves 22a and 22b are similarly composed of circular thin plates made of synthetic resin. The upper parts thereof are fixed by fusing to the upper parts of the left and right closure walls 14a and 15a surrounding the circular ports of the inner end portions of the waste fluid outflow passages 17a and 17b, so that the left and right waste fluid outflow passages 17a and 17b may be closed normally by hanging the lower parts of the normally closed type valves plates 22a and 22b. The normally closed type valves 22a and 22b may be opened by the pushing force generated at the time of the contraction of the elastic containers 10 and 11 caused by the positive pressure of the atmospheric air introduced therein.

It is preferable that the waste fluid discharging tubes 19a and 19b, the waste fluid suction tubes 18a and 18b, and the waste fluid suction tube 18 are all made of transparent synthetic resins so that the waste fluid flowing through these tubes can be seen from the outside. Also, the length of each of the waste fluid suction tubes 18a and 18b is sufficient with 30 cm or less and the length of the single waste fluid suction tube 18 is enough with 2–3 meters from a standpoint of convenient use thereof, but, of course, it is not limited thereto.

In addition, it is preferable that the outer end portions of the left and right waste fluid suction tubes 18a and 18b and a base end portion of the single waste fluid suction tube 18 are connected by a T-shaped connecting tube 28 which is inserted therein and that nonreturn valves 28a and 28b are interposed respectively in the outer end portions of the left and right waste fluid suction tubes 18a and 18b. Furthermore, it generally is convenient to mark graduations 29 on the surface of the waste fluid storing container 20.

Thus, the suction system body P1 and the waste fluid system body P2 are manufactured as components for assembling a suction unit P together. At the time of using the suction unit P, the suction unit according to the present invention can be assembled simply by mounting the peripheral surfaces of the enclosure walls 14a and 15a of the left and right closing members 14 and 15 of the waste fluid system constructional body P2 in the openings of the left and right chambers 6 and 7 of the suction system body P1.

Furthermore, the suction unit P according to the present invention is preferably used such that, as shown in FIG. 2 and FIG. 3, the waste fluid storage container 20 of the waste fluid system body P2 is hung on the stand 30. The stand 30 may be made of any desired type of metals, wood, synthetic resins or the like, and is composed of a base plate 30a, a thick and square pillar 30b vertically extending from the base plate 30, an arm rod 30c which extends horizontally and forwards at a predetermined height from the front surface of the pillar 30b. The arm rod 30c has a length that provides a space beneath which is enough to accommodate waste fluid storage container 20 which is bulged with the expected maximum amount of the waste fluid stored therein. The stand 30 further includes a hanging support plate 30d which is attached to the forward end portion of the arm rod 30c and extends horizontally and crossing the arm rod 30c. A pair of hanging metal hooks 30e and 30e are attached to the left and right portions of the support plate 30d. The top surface of the square pillar 30b is formed into a rectangular cavity 31 for mounting the reciprocating-type change-over suction device 1 of the suction system body P1, as clearly shown in FIG. 4. In order to allow the stand 30 to be movable, four castors 32 are attached to the corners of the lower surface of the base plate 30a.

In addition, a rectangular protrusion 33 made of metal is formed integrally with the reciprocating type suction change-over suction device 1 so as to project from the bottom surface thereof. The protrusion 33 is adapted to be mounted in the foregoing rectangular cavity 31 of the stand 30, and is secured to the square pillar 30b by inserting a pair of screws 34a and 34b through left and right holes in a rear side wall of a square wall surrounding the mounting square cavity 31 and then screwing the pair of screws into left and right threads in the rear surface of the mounting rectangular protrusion 33. Thus, the suction body P1 is installed on the stand 30, and then the foregoing bag type container 20 is hung on the stand by hanging left and right hanging holes 35a and 35b out to the heat sealed band part 20a on the left and right hooks 30e and 30e. The suction unit for medical use according to the present invention then is ready for use.

When the vacuum pump is operated and the forward end of the waste fluid suction tube 18 is applied onto a lesion or affected part of a patient, the leftward and rightward movements of the reciprocating type change-over suction device 1 are repeated as explained below. Consequently, the waste fluid on the lesion is sucked, collected and discharged alternatively at the left side and right side by the alternate and reciprocal expansion and contraction of the left and right elastic containers 10 and 11 so that collected waste fluids in the left and right elastic containers 10 and 11 are stored into the waste fluid storing container 20 by passage through the left and right waste fluid discharging tubes 19a and 19b. The movement of the left and right elastic containers 10 and 11, the inflow of the waste fluids in the tubes 18, 18a and 18b, the discharging flow of the waste fluids in the left and right waste fluid discharging tubes 19a and 19b and the amount of the waste fluid in the waste fluid storage container 20 can be confirmed respectively by observation through the transparent left and right chambers 6 and 7, the transparent tubes 18, 18a and 18b, the transparent tubes 19a and 19b and the transparent storage container 20. Thus, since the vacuum pump M is isolated completely from the waste fluid system body P2, the vacuum pump M is not contaminated with the waste fluid and also the surrounding atmosphere is not contaminated therewith. Therefore, the suction, collection and storage of the waste fluid from the patient can be carried out smoothly and sanitarily.

When a predetermined amount of the waste fluid is stored in the container 20, the container 20 is removed from the hooks 30e and 30e. Also, the left and right closing members 14 and 15 are detached from the chambers 6 and 7, and the waste fluid system body P2 can be disposed. Since the waste fluid system body P2 is a closed system in which any remaining waste fluid is confined therein, a person safely can dispose of the waste fluid system body without contacting the waste fluid. Then, the left and right closing members of a new waste fluid system body P2 are securely mounted in the openings of the left and right chambers 6 and 7 of the reciprocating type change-over suction device 1 on the stand 30 and a new waste fluid storage container 20 is hung on the hooks 30e and 30e so as to be ready for the next use.

When a molded hard box type container 20 made of plastic or glass is used instead of the soft bag type container, the base plate 31b has a support area wide enough to place the container thereon. Consequently, such a container 30 may be used simply by placing it thereon and the hanging structures such as the arm rod 30c and the hooks 30e and 30e on the stand 30 side are not required.

Preferably, the height of the stand 30 is approximately equal to that of a bed of the patient at the highest level from the floor, for instance, about 70 cm. The height of the suction change-over device 1 is generally lower than the height position of the patient, and is, for instance, generally 50–70 cm in height. Thus, when the suction operation is stopped, the waste fluid sucked from the lesion of the patient is prevented from flowing backwards to the lesion.

Further, a length of each of the left and right waste fluid suction tubes 18a and 18b is sufficient at about 1–2 m. As an occasion demands, the stand may be moved to near or the lesion to be sucked, so that the suction operation is facilitated. A length of each of the left and right discharging tubes 19a and 19b is sufficient at about 20–32 cm. In the illustrated embodiment, a bag type container 20 having a volume of 3 liters is used.

Next, the construction and operation of the reciprocating type change-over suction device 1 of the suction unit P will be explained more greater in detail with reference to FIGS. 6(a), (b) and (c). The cylinder 1 is longer than the cylinder holding tubular body 1a, and the ventilation passages 4 and 5 on the left side and the right side thereof are made as described below. The left ventilation passage 4 comprises an air hole 4a which is in the radial direction and can be bought in and out of communication with a portal 2a1 of the left branch passage 2a, an air hole 4b which is made in the radial direction and can be brought in and out of communication with the left chamber 6, and an axial communication passage 4c which extends between these air holes 4a and 4b. The right ventilation passage 5 comprises an air hole 5a which is made in the radial direction and can be brought in and out of communication with a port 2a1 of the right passage 2b, an air hole 5b which can be in and out of communication with the right chamber 7, and an axial communication passage 5c which extends between these air holes 5a and 5b. The cylinder 1b slidably held leftwards and rightwards by the cylinder holding tubular body 1a, in the first position, as shown in FIG. 6(a), for example, is biased in position on the left side that the left end portion thereof projects from the left end surface of the cylinder holding tubular body 1a thereof and the air hole 4b thereof is exposed in the interior of the left 5 chamber 6. At the same time, the air hole 4a thereof is in communication with the port 2a1 of the left branch passage 2a. Accordingly, the left chamber 6 is in communication with the left air passage 2a through the communication passage 4c while the right end portion of the cylinder 1b is retracted into the right end portion of the cylinder holding tubular body 1a. Further, the air hole 5a of the right ventilation passage 5 is not in communication with the port 2b1 of the left branch passage 2b and the air hole 5b is not exposed to the interior of the right chamber 7 and is not in communication with the port 2b1 of the right branch passage 2b.

It is of course apparent that, in the first position, the cylinder 1b may be biased to the right side which is reverse to the above-mentioned left-biased position. More in detail, the cylinder 1b, in the first position, is so biased on the right side that the right end portion thereof projects from the right end surface of the cylinder holding tubular body 1a so that the air hole 5b is exposed to the interior of the right chamber 7. At the same time, the air hole 5a of the right ventilation passage 5 is in communication with the port 2b1 of the right branch passage 2b. Accordingly, the right chamber 7 is in communication with the right branch passage 2b through the communication passage 5c, while the left end of the cylinder 1b is retracted into the cylinder holding tubular body 1a. Further, the air hole 4a of the left ventilation passage 4 is not in communication with the port 2a1 of the left branch passage 2a and the left ventilation passage 4 is not in communication with the left chamber 6 and the left branch passage 2a.

In order to achieve such a condition where the left branch passage 2 and the left chamber 6 are not in communication one with another and the right branch passage 2b and the right chamber 7 are not in communication with one another, or vice versa, it is necessary that the ventilation passages 4 and 5 in the cylinder 1b are positioned at the left side and at the right side of the middle of the length of the cylinder and that the distance between the air hole 4a and the air hole 4b of the ventilation passage 4 and the distance between the air hole 5a and the air hole 5b of the ventilation passage 5 are unequal. In the illustrated embodiment, the distance of the former is greater than the distance of the latter. For example, the distance between the air holes 4a and 4b may be 28 mm and the distance between the air holes 5a and 5b may be 25 mm.

In a case where the cylinder 1b has a circular cross-section, it is a possibility that, during repeated reciprocal leftward and rightward movements thereof, the air holes 4a and 4b will tend to be displaced in the circumferential direction and cause nonalignment with the ports 2a1 and 2b1 of the corresponding branch passages 2a and 2b. In order to avoid such a possibility, it is preferable that the cylinder 1b have annular grooves 4a1 and 5a1 which communicate with the corresponding air holes 4a and 5a and have a width equal to or greater than the diameter of the air holes 4a and 5a. Thereby, the foregoing possibility is estimated and it is assured that, even when the air holes 4a and 5a are displaced, circumferentially, to be in nonalignment with the respective ports 2a1 and 2b1, they always maintain communication with the corresponding branch passages 2a and 2b through the respective annular grooves 4a1 and 5a1. In the illustrated embodiment, the width of the annular grooves 4a1 and 5a1 is equal to the diameter of the air holes 4a and 5a. In addition, both end portions of the cylinder 1b are also provided with similar annular grooves 4b 1 and 5b 1 which communicate with the air holes 4b and 5b and have a width equal to the diameter of the corresponding air holes 4b and 5b. Thereby, the air in the corresponding chambers 6 and 7 can flow easily and efficiently through the annular grooves 4b1 and 5b1 into the air holes 4b and 5b for a predetermined period of time.

Furthermore, in the illustrated embodiment, when the cylinder 1b is moved alternately to the left and the right, the right actuation plate 9 and the left actuation plate 8 alternately collide with the right end surface and the left end surface of the cylinder holding tubular body 1a and, at the same time, the normally closed type valves 12 and 13 corresponding thereto are opened alternately which thereby allows atmospheric air to flow into the chamber 6 and the chamber 7 alternately.

In the operation of the reciprocating-type change-over suction device 1, the alternate operation of the left chamber 6 and the right chamber 7 to alternately become a negative by pressure or a positive pressure in accordance with the reciprocation thereof, the alternate operation of expansion and contraction of the left elastic container 10 and the right elastic container 11 are carried out in conjunction therewith. The alternate operation of collection and discharge of the waste fluid from a patient which is carried out in conjunction with the alternate expansion and contraction of the left elastic container 10 and the right elastic container 11 is explained with reference with FIG. 6.

In particular, FIG. 6(a) is a sectional view of an important part of the suction unit P showing the cylinder 1b of the suction change-over device 1 positioned at the extreme left end. FIG. 6(b) is a diagram showing respective steps of communication of the respective air holes 4a, 4b and 5a, 5b of the left and right ventilation passages 4 and 5 with the left and right branch passages 2a and 2b and the left and right chambers 6 and 7 made in the course of moving or shifting the cylinder 1 from the extreme left end to the extreme right end. FIG. 6(c) is a sectional view of the important part of the suction unit P showing when the cylinder 1b of the suction change-over device 1 is positioned at the extreme right end.

Further, in FIG. 6(a) and FIG. 6(c), the abbreviation "P.P." stands for a positive pressure and the abbreviation words "N.P." stands for a negative pressure. In FIG. 6(b), the symbols a, b, c, d represent the respective shifted positions of the cylinder 1b and the symbols (1), (2), (3) and (4) represent the respective states of communication and non-communication of the air holes 4b, 4a, 5a and 5b of the cylinder 1b with the branch passage 2a and branch passage 2b at the respective shifted positions a, b, c and d of the cylinder 1b.

As shown in FIG. 6(a), when the cylinder 1b is positioned at the extreme left end before the start of the operation of the vacuum pump, the left chamber 6 is shut off from the atmosphere and accordingly is maintained as a closed chamber and the elastic container 10 is kept in a contracted condition by the air pressure confined in the closed chamber. The right chamber 7 has a positive pressure of the atmosphere compressing the elastic container 11 as shown by an arrow because the actuation plate 9 is positioned to push and open the normally closed type valve 13 and allow the atmosphere to flow into the chamber 7. Consequently, the elastic container 11 is maintained in a contracted state as shown by an arrow.

The air holes 4a, 4b, 5a, and 5b of the cylinder 1b at this extreme left end position as shown in FIG. 6(a), namely, at a start position a-(1) in FIG. 6(b), are located at a position that the air hole 4a of the left air passage 4 is in alignment with the left branch passage 2a, the air hole 4b is exposed to the interior of the left chamber 6 and is in communication therewith. Consequently, the left chamber 6 is in communication with the branch passage 2a through the left ventilation passage 4, while the air hole 5a of the right ventilation passage 5 is in nonalignment with the right branch passage 2b and the air hole 5b is retracted in the cylinder holding tubular body 1a and is not exposed to the interior of the right chamber 7. Thus, communication between the right chamber 7 and the right branch passage 2b through the right ventilation passage 5 is shut off.

In FIG. 6(b), the communication of the four air holes 4a, 4b, 5a and 5b of the cylinder 1bwith the respectively corresponding left branch passage 2b, the left chamber 6, the right branch passage 2b and the right chamber 7 are indicated by white circles and the non-communication thereof are indicated by black circles. At the foregoing position of the cylinder, when the vacuum pump is actuated, a suction force is applied to the interior of the left chamber 6 through the left branch passage 2a and the left ventilation passage 4 to remove the air therefrom, so that a negative pressure is produced in the left chamber 6. Thereby, the elastic container of bellows type 10 is expanded as shown in the arrow direction and is suddenly increased in volume. Accordingly, a negative pressure is produced in the waste fluid suction tubes 18, 18a which have been applied to the lesion of a patient and the waste fluid is sucked therefrom and collected into the expanded elastic container 10.

Meanwhile, the elastic container 10 being expanded pushes the operation plate 6 rightwards in the drawing, and at the same time the cylinder 1b connected thereto is shifted rightwards. Accordingly, the air holes 4a, 4b, 5a and 5b are also shifted rightwardly, and when the cylinder 1b is shifted rightwards from the foregoing start position a-(1) to the first shift position as denoted by b-(2) in FIG. 6, for instance, shifted 5 mm from the a position to the b position as shown in FIG. 6, the communication between the air holes 4a and 4b and the left branch passage 2a is maintained continuously. During the above, the exhausting operation by the vacuum pump is carried out continuously, the negative pressure in the left chamber 6 is maintained continuously, and the non-communication of the air holes 5a and 5b with the right branch passage 2b and the right chamber 7 is still maintained.

Furthermore, when the cylinder 1bis shifted rightwardly 5 mm from position b to a position c, that is, the second shift position as shown by c-(3) in FIG. 6(b), communication of the air hole 4a with the left branch passage 2a is shut off. At the same time, the air hole 4b is retracted into the cylinder holding tubular body 1a and the communication thereof with the left chamber 6 is shut off. Thus, the left chamber 6 and the left branch passage 2a are in communication with each other, but the negative pressure in the left chamber 6 is maintained. Meanwhile, the air hole 5a begins to be in communication with the right branch passage 2b and the air hole 5b is exposed to the interior of the right chamber 7. Thus, there is communication between the right chamber 7 and the right branch passage 2b through the air passage and, accordingly, the suction operation of the vacuum pump on the right chamber 7 begins. However, during the rightward movement of the cylinder 1b from the first shift position to the second shift position, the right actuation plate 9 connected thereto is shifted rightwards, but does not depart from the valve rod 13a of the normally closed type valve 13. Accordingly, communication of the chamber 7 with the atmosphere is maintained and the positive pressure in the chamber 7 is maintained.

Next, when the cylinder 1b is further shifted rightwardly 5 mm from the position c to the extreme right end position d, that is, to the third shift position as shown by d-(4) in FIG. 6(b), the left actuation plate 8 in the left chamber 6 pushed further by the successive expansion of the elastic container 10 pushes the valve rod 12 of the closed valve 12 and opens the valve 12. Thus, the atmosphere flows into the chamber 6 as shown in FIG. 6(c), so that the interior of the left chamber 6 is given a positive pressure. Also, the expanded elastic container 10 is compressed by the positive pressure of the atmosphere, so that the waste fluid in the elastic container 10 is pushed outwards and discharged therefrom through the waste fluid outflow passage 17a and the waste fluid discharging tube 19 and is stored in the waste fluid storing container 20.

On the other hand, the right operation plate 9 in the right chamber 7 is further shifted rightwardly and departs from the valve rod 13a of the normally closed type valve 13 so that the valve 13 is automatically closed by the spring force thereof. Therefore, the interior of the right chamber 7 is shut off from the atmosphere, and consequently the interior of the right chamber 7 is evacuated by the successive suction operation of the vacuum pump, and is given a negative pressure. The elastic container 11, which has been under a compressed state by the positive pressure, is expanded by the negative pressure, and the expanded elastic container 11 collides with the right actuation plate 9 and pushes it in the arrow direction as shown in FIG. 6(c). At the same time, the cylinder 1b together with the actuation plate 9 are pushed leftwards. Simultaneously, the waste fluid of the patient is sucked and collected in the elastic container 11 through the waste fluid suction tubes 18 and 18b and the waste through inflow passage 19b by the negative pressure produced by the expansion of the elastic container 11.

Thus, the cylinder 1b is shifted leftwardly through positions d, c, b, a as shown in FIG. 6(b). When the cylinder is shifted to the extreme left end position a, the right actuation plate 9 is positioned again as shown in FIG. 6(a) and pushes and opens the normally closed type valve 13 again, so that the atmosphere flows into the right chamber 7. The atmosphere compresses the expanded elastic container 11 and pushes the waste fluid contained in the elastic container 11 outwardly and the waste fluid is stored in the waste fluid storing container 20 through the waste fluid outflow passage 17b and the waste fluid discharging tube 19b. On the other hand, in conjunction the leftward movement of the cylinder 1b, the left actuation plate 8 departs from the valve rod 12a of the normally closed type valve 12, and the valve is automatically closed by its spring. The left chamber becomes a closed chamber confining the atmosphere, and, at the same time, communicates with the vacuum pump again, and is evacuated by the exhausting operation of the vacuum pump to produce the negative pressure therein. Thus, by the repetition of the leftward and rightward movements of the cylinder 1bthereafter, the above mentioned successive operations, namely, the expansion and contraction of the left and right elastic containers 10 and 11 are repeated alternately so that suction collection and discharge of the waste fluid are repeated alternately and continuously.

Furthermore, the reciprocating type change-over suction device 1 may be constructed such that the axial hole 3 of the center of the cylinder holding tubular body 1a is a square in cross section, and the cylinder 1ba square in cross section is slidably inserted therethrough. In this situation, the cylinder 1bcannot rotate in the circumferential direction, and, accordingly, it is not necessary to have annular grooves 4a1 and 5a1 to communicate with the air holes 4a and 5a.

Thus, according to the present invention, since the suction force of the suction apparatus is not exerted on the waste fluid storing container, the problems associated with the conventional suction unit for medical applications can be reduced or even eliminated. In addition, the suction of a waste fluid from a patient and storage thereof in the waste fluid storage container can be carried out sanitarily and continuously for a desired time without contamination of the environment.

According to the invention, the suction unit can be constructed simply by assembling the suction system body and the waste fluid system body together, and the unit is simple and easy to use after completion of the assembly thereof. Also, the waste fluid system body can be easily removed from the suction system body, and can be disposed safely without the possibility of pollution with the waste fluid.

According to the invention, even when the cylinder is rotated in the circumferential direction, communication of the left and right air holes with the left and right branch passages respectively can be assured by the corresponding annular grooves.

According to the invention, the suction unit can be used by mounting it on a stand in a stable manner.

According to the invention, as the amount of the waste fluid stored in the waste fluid storage container increases, only air which does not contain harmful substances as contained in the container is discharged to the outside through the filter, and the waste fluid can be stored up to a predetermined amount smoothly and safely without leakage of the waste fluid. According to the invention, the disposable waste fluid storage container can be attached to and detached from the stand.

What is claimed:

1. A suction unit for medical applications comprising a reciprocating type change-over suction device, the suction device composed of a cylinder holding tubular body which is provided with a single passage and left and right branch passages bifurcated from the single passage for connecting a suction apparatus, a cylinder which is held slidably by the cylinder holding tubular body and which is provided with left and right ventilation passages, left and right closed chambers respectively connected to left and right end portions of the cylinder holding tubular body, left and right elastic containers which respectively are contained in the left and right closed chambers and which have opening edges airtightly respectively attached to inner surfaces of left and right closing members, left and right actuation plates which respectively are connected to the left and right end portion of the cylinder and contained in the left and right closed chambers, left and right normally-closed type valves respectively installed on the left and right closed chambers, left and right waste fluid suction tubes which respectively are connected at one end portion thereof to left and right waste fluid inflow passages, respectively penetrating the left and right closing members and at another end portion thereof to a single waste fluid suction tube, and left and right waste fluid discharging tubes which are respectively connected at one end portion thereof to left and right waste fluid outflow passages respectively in the left and right closing members and at another end portion thereof to a waste fluid storage container.

2. A suction unit for medical applications to claim 1, the unit comprising an assembly composed of bodies (a) and (b) as follows:
    (a) a suction-system body comprising the suction device, the left and right actuation plates respectively connected to the left and right end portions of the cylinder, the left and right chambers which respectively are composed of left and right end plates and left and right transparent cylindrical walls attached at inner end portions thereof to the left and right end walls to form left and right chambers of which mouths are open at outer sides thereof, and the left and right normally closed type valves respectively are connected at one end portion thereof to the left and right closing members and at the other end portions of the single suction tube.

3. A suction unit for medical applications according to claim 2, wherein the cylinder is provided with annular grooves which communicate with left and right air holes.

4. A suction unit for medical applications according to claim 3, wherein the unit is mounted on a stand.

5. A suction unit for medical applications according to claim 4, wherein the waste fluid storage container is a disposable container, and a closed upper end portion of the waste fluid storage container is provided with a filter.

6. A suction unit for medical applications according to claim 2, wherein the disposable container is made of a synthetic resin and comprises a bag type container which has a capacity in the range of from 3000 ml to 8000 ml, graduations on the surface thereof, and plural number of hanging holes through a long and narrow sealed portion provided at an upper portion thereof.

7. A suction unit for medical applications according to claim 2, wherein the unit is mounted on a stand.

8. A suction unit for medical applications according to claim 7, wherein the waste fluid storage container is a disposable container, and a closed upper end portion of the waste fluid storage container is provided with a filter.

9. A suction unit for medical applications according to claim 1, wherein the cylinder is provided with annular grooves which communicate with left and right air holes.

10. A suction unit for medical applications according to claim 9, wherein the disposable container is made of a synthetic resin and comprises a bag type container which has a capacity in the range of from 3000 ml to 8000 ml, graduations on the surface thereof, and a plural number of hanging holes through a long and narrow sealed portion provided at an upper portion thereof.

11. A suction unit for medical applications according to claim 9, wherein the unit is mounted on a stand.

12. A suction unit for medical applications according to claim 11, wherein the waste fluid storage container is a disposable container, and a closed upper end portion of the waste fluid storage container is provided with a filter.

13. A suction unit for medical applications according to claim 1, wherein the unit is mounted on a stand.

14. A suction unit for medical applications according to claim 4, wherein the waste fluid storage container is a disposable container, and a closed upper end portion of the waste fluid storage container is provided with a filter.

* * * * *